(12) United States Patent
Weber et al.

(10) Patent No.: US 7,472,932 B2
(45) Date of Patent: Jan. 6, 2009

(54) LUER-LOCK CONNECTOR FOR MEDICAL DEVICES

(75) Inventors: Jörg Weber, Edling (DE); Bernd Beck, Rangendingen (DE)

(73) Assignee: Smiths Medical Deutschland GmbH, Kirchseeon (DE)

( * ) Notice: Subject to any disclaimer, the term of this patent is extended or adjusted under 35 U.S.C. 154(b) by 0 days.

(21) Appl. No.: 11/201,530

(22) Filed: Aug. 11, 2005

(65) Prior Publication Data
US 2006/0033334 A1 Feb. 16, 2006

(30) Foreign Application Priority Data
Aug. 12, 2004 (DE) .................. 20 2004 012 714 U

(51) Int. Cl.
*F16L 25/00* (2006.01)
(52) U.S. Cl. .................. 285/386; 285/110; 285/332; 285/354
(58) Field of Classification Search .................. 285/110, 285/332, 354, 386
See application file for complete search history.

(56) References Cited

U.S. PATENT DOCUMENTS

| 4,360,024 A | | 11/1982 | Wallace | |
|---|---|---|---|---|
| 4,452,473 A | | 6/1984 | Ruschke | |
| 4,639,019 A | * | 1/1987 | Mittleman | 285/332 |
| 4,824,145 A | * | 4/1989 | Carlsson | 285/38 |
| 5,047,021 A | * | 9/1991 | Utterberg | 604/533 |
| 5,113,571 A | * | 5/1992 | Manska | 29/453 |
| 5,591,143 A | | 1/1997 | Trombley, III et al. | |
| 5,984,373 A | * | 11/1999 | Fitoussi et al. | 285/92 |
| 6,364,869 B1 | | 4/2002 | Bonaldo | |
| 6,843,513 B2 | | 1/2005 | Guala | |
| 6,893,056 B2 | | 5/2005 | Guala | |
| 2002/0115984 A1 | | 8/2002 | Guala | |

FOREIGN PATENT DOCUMENTS

| DE | 201 09 061 U1 | 5/2001 |
|---|---|---|
| DE | 103 03 381 A1 | 8/2003 |
| DE | 103 10 469 A1 | 10/2003 |
| EP | 0 411 521 A1 | 2/1991 |
| EP | 1 236 481 B1 | 10/2004 |
| WO | WO 02/096500 A1 | 12/2002 |
| WO | WO 2004/027305 1 | 4/2004 |

* cited by examiner

*Primary Examiner*—Aaron M Dunwoody
*Assistant Examiner*—Fannie Kee
(74) *Attorney, Agent, or Firm*—Senniger Powers LLP

(57) ABSTRACT

A Luer-Lock connector for medical devices with a tubular body and a swivel nut enclosing it and secured on it. The swivel nut has a radially inward-protruding edge and the tubular body has at least one radially outward-protruding elastic arm, whose end can be stopped against the edge.

4 Claims, 1 Drawing Sheet

LUER-LOCK CONNECTOR FOR MEDICAL DEVICES

FIELD OF THE INVENTION

The invention pertains to a Luer-Lock connector for medical devices.

BACKGROUND OF THE INVENTION

This type of Luer-Lock connector is known from DE 103 03 381 A1. This Luer-Lock connector, as is also generally common in medical technology, has a tubular body and a swivel nut with an inside thread secured on it and enclosing it, which thread engages in the outside thread of a Luer-Lock mating element. Ordinarily the swivel nut is applied to the so-called male Luer-Lock part. During assembly, it is pushed on from the free end of the tubular body and is necessarily widened a certain degree in so doing. Even if one remains fully within the elastic range, the swivel nut, after assembly, can be pushed down again by corresponding expansion, so that an unreleasable fastening of the swivel nut is scarcely possible after being pushed on.

In order to avoid sliding down of the swivel nut during tensile stress, as occurs during tightening, an edge is applied to the swivel nut and the tubular body, the two edges serving as a stop against pulling down. Such edges can secure the swivel nut relatively well in practice. However, if the material is plastically expanded during pushing-on of the swivel nut, this edge cannot guarantee secure fastening of the swivel nut. Another drawback of such an edge is that the swivel nut can be arbitrarily rotated farther, since it is not pulled into a cone that would lead to locking or fastening of the swivel nut. During further rotation of the swivel nut, the female Luer connector is invariably pulled onto the male Luer cone. Because of this, significant stresses develop in the female Luer connector, which can rapidly lead to material failure, like stress cracks or leaks. Another drawback of an edge is that, with insufficient fastening of the swivel nut or unduly smooth surfaces of the threads, there is a hazard that the swivel nut will automatically rotate back and the entire connection will loosen. This is further promoted by lubricants or liquids.

In DE 103 03 381 A1, a cone is present between the swivel nut and the male Luer cone, which causes widening during pushing-on of the swivel nut, and especially of its radially inward-protruding edge, and therefore increases the risk that the swivel nut can be pulled from the tubular body.

A Luer-Lock connector, in which two parts, rotatable relative to each other, can be fastened to each other by stop edges in the axial direction, is also known from U.S. Pat. No. 6,364,869 B1. Here again, however, a slope is provided, which can cause widening of the outer part during pushing-together of the parts.

SUMMARY OF THE INVENTION

An object of the invention is a Luer-Lock connector that guarantees secure holding of the swivel nut on the tubular body, although assembly also occurs by pushing together the swivel nut and the tubular body.

Briefly, therefore, the invention is directed to a Luer-Lock connector for medical devices with a tubular body and a swivel nut enclosing it and secured on it, characterized by the fact that the swivel nut has a radially inward-protruding edge, and that the tubular body has at least one radially outward-protruding elastic arm, whose end can be stopped against the edge.

Other objects and features will be in part apparent and in part pointed out hereinafter.

DETAILED DESCRIPTION OF THE PREFERRED EMBODIMENTS

Figure 1:
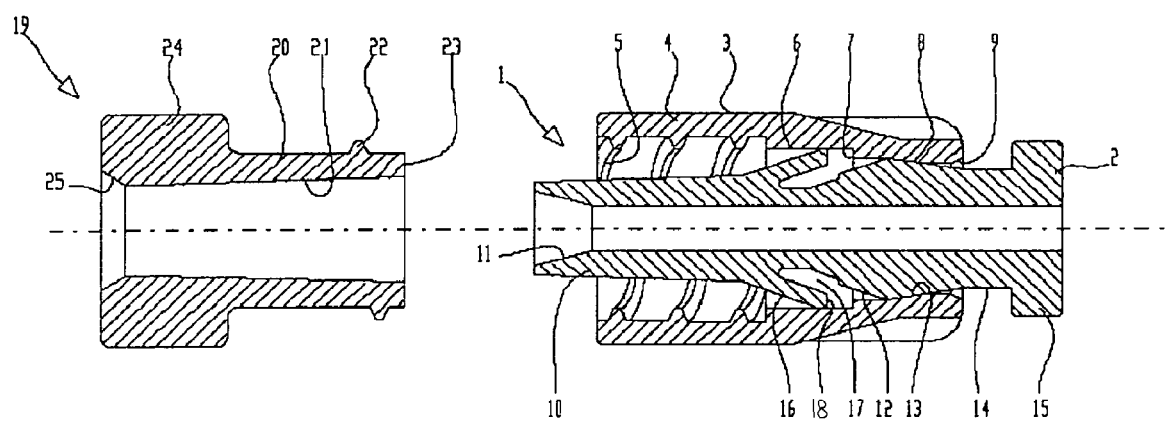
FIG. 1 shows a longitudinal section of a Luer-Lock connector according to the invention.

This application claims priority from German application 20 2004 012 714.8, filed Aug. 12, 2004, the entire disclosure of which is expressly incorporated herein by reference.

The basic principle of the invention consists of the fact that at least one spring element is provided that is elastically deformed when the two parts are pushed together and, after the pushing together, widens and serves as a stop against the sliding-down of the swivel nut from the tubular body.

Two or more elastic arms are preferably used, which are mounted on the tubular body and are arranged to protrude radially outward. Their ends stop against the swivel nut with an edge.

A cone seat can then be provided between the swivel nut and tubular body. Even if this is widened when the two parts are pushed together, the elastic arms are widened much more and always reliably stopped with the edge.

The Luer-Lock connector has a first connector part, which is ordinarily referred to as the male Luer-Lock connector and carries the reference number 1. This connector has a tubular body 2 and a rotatable swivel nut 3 partially surrounding it, which has a widened part 4 with greater diameter, provided with inside thread 5. A narrowed part 6 with a smaller diameter is connected to this, which ends on a radially inward-protruding edge 7. From there, a sealing cone 8 is connected, optionally via a cylindrical part, which continuously decreases in diameter to the end facing away from thread 5, until it opens on the rear end of swivel nut 3 via a bevel 9.

The tubular body 2 has a Luer cone 10 on its front end, on whose front end an inner cone 11 is present. On the rear end of Luer cone 10, at least two elastic arms 16 are mounted that protrude radially outward. Their rear edge 18 then forms a stop with edge 7 of the swivel nut. Between the material of the tubular body 2 and the elastic arm 16, an annular space 17 is therefore formed in which the elastic arm 16 can engage. A sealing cone 13 connected to this annular space via a slope 12, is fit onto the sealing cone 8 of the swivel nut. A cylindrical section 14 and an end piece 15 are connected to this cone 13.

During assembly, the tubular element 2 is pushed with the free end of Luer cone 10 into the rear end of the swivel nut on bevel 9. The elastic arms 16, upon sliding past cone 8, can engage inward in the annular space 17 and, after they have slid past the edge 7, rebound outward against the inside wall of the narrowed part 6. Upon further introduction, the cone 8 of the swivel nut 3 is widened by the slopes 12 and cone 13, until the two parts are pushed into each other. Even if a plastic, i.e., permanent deformation, i.e., widening of the swivel nut, occurs here, the edge 7 is still effective as a stop for the end 18 of the elastic arm 16, so that even after widening, a secure and unreleasable connection is present between the swivel nut and the tubular body.

In the interest of completeness, the Luer-Lock mating piece 19 is also shown in FIG. 1, which is designated as the female Luer-Lock part. It also has a tubular body 20 with an inside cone 21 adapted to the Luer cone 10. On its outer periphery, an outside thread 22 is provided, which cooperates with the inside thread 5 of the swivel nut. A front edge 23 of the mating piece forms its front end. Since the two cones 10 and 21 engage one inside the other, the swivel nut 3, during tightening, can be pushed forward toward the free end of Luer cone 10, so that, on the one hand, the seal between the cone 8 and cone 13 is effective, and, on the other hand, widening between these two cones can also occur. However, the stop between the elastic arm 16 and edge 7 comes into play here, which prevents further displacement and, therefore, pulling-off of the swivel nut.

The female Luer-Lock part 19 has a widened gripper part 24 and a bevel 25 on its rear end for connection of a medical device, a medical tube or other object.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods and products without departing from the scope of the invention, it is intended that all matter contained in the above description and shown in the accompanying drawings shall be interpreted as illustrative and not in a limiting sense.

What is claimed is:

1. Luer-Lock connector for medical devices comprising:
a first connector part having:
a tubular body;
a swivel nut enclosing the tubular body and rotatably secured to the tubular body;
wherein the swivel nut has an inside wall, a radially inward-protruding edge, and an inside thread; and
a radially outward-protruding elastic arm on the tubular body which during assembly of the swivel nut onto the tubular body rebounds outwardly against said inside wall of the swivel nut and forms a stop against the radially inward-protruding edge on the swivel nut to prevent pulling off of the swivel nut during operation of the luer-lock connector in a direction opposite to the direction of assembly of the swivel nut onto the tubular body;
wherein the swivel nut and the tubular body each have a sealing cone, and wherein said sealing cone of the tubular body is fitted onto the sealing cone of the swivel nut to form an effective seal;
and a second connector part having an outside thread adapted to fit into the inside thread of said first connector part.

2. The Luer-Lock connector according to claim 1 wherein the tubular body has two or more elastic arms.

3. The Luer-Lock connector of claim 2 wherein the two or more elastic arms are arranged such that during assembly of the swivel nut onto the tubular body they are biased radially inwards by the cone of the swivel nut and released outwardly after said arms pass said radially inward-protruding edge on the swivel nut.

4. The Luer-Lock connector of claim 1 wherein the sealing cone of the swivel nut continually decreases in diameter toward a rear end of the swivel nut into which the tubular body is pushed during assembly of the swivel nut onto the tubular body.

* * * * *